US010322032B2

(12) United States Patent
Scavone et al.

(10) Patent No.: US 10,322,032 B2
(45) Date of Patent: *Jun. 18, 2019

(54) ABSORBENT ARTICLE COMPRISING A FRAGRANCE OR ODOR CONTROL COMPOSITION

(71) Applicant: The Procter & Gamble Company, Cincinnati, OH (US)

(72) Inventors: Timothy Alan Scavone, Loveland, OH (US); Misael Omar Aviles, Cincinnati, OH (US); Peter Christopher Ellingson, Symmes Township, OH (US); Dean Larry Duval, Lebanon, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 872 days.

This patent is subject to a terminal disclaimer.

(21) Appl. No.: 14/308,764

(22) Filed: Jun. 19, 2014

(65) Prior Publication Data

US 2014/0378921 A1 Dec. 25, 2014

Related U.S. Application Data

(60) Provisional application No. 61/836,788, filed on Jun. 19, 2013.

(51) Int. Cl.
| | | |
|---|---|---|
| A61F 13/00 | (2006.01) | |
| A61F 13/15 | (2006.01) | |
| A61F 13/58 | (2006.01) | |
| A61L 15/46 | (2006.01) | |

(52) U.S. Cl.
CPC .. *A61F 13/00063* (2013.01); *A61F 13/15756* (2013.01); *A61F 13/58* (2013.01); *A61L 15/46* (2013.01); *A61L 2300/10* (2013.01); *A61L 2300/216* (2013.01); *Y10T 156/10* (2015.01)

(58) Field of Classification Search
CPC .......... A61F 13/00063; A61F 13/15756; A61F 2013/51076; A61F 2013/5109; A61F 13/8405; A61F 2013/8408; A61F 2013/8452; A61L 15/46
See application file for complete search history.

(56) References Cited

U.S. PATENT DOCUMENTS

| | | | |
|---|---|---|---|
| 3,654,929 A * | 4/1972 | Nilsson ............. | A61F 13/15211 604/364 |
| 4,460,364 A * | 7/1984 | Chen ....................... | A61L 15/58 229/245 |
| 4,540,721 A | 9/1985 | Staller | |
| 4,973,422 A | 11/1990 | Schmidt | |
| 5,331,015 A | 7/1994 | DesMarais et al. | |
| 5,387,207 A | 2/1995 | Dyer et al. | |
| 5,543,157 A | 8/1996 | Trinh et al. | |
| 5,550,167 A | 8/1996 | DesMarais | |
| 5,571,782 A | 11/1996 | Trinh et al. | |
| 5,591,146 A * | 1/1997 | Hasse ................. | A61F 13/5611 604/359 |
| 6,024,943 A | 2/2000 | Ness et al. | |
| 6,042,792 A | 3/2000 | Shefer et al. | |
| 6,051,540 A | 4/2000 | Shefer et al. | |
| 6,458,754 B1 | 10/2002 | Velazquez et al. | |
| 6,531,444 B1 | 3/2003 | Shefer et al. | |
| 7,316,994 B2 | 1/2008 | Jordan et al. | |
| 7,365,043 B2 | 4/2008 | Baker et al. | |
| 8,187,580 B2 | 5/2012 | Dykstra et al. | |
| 2004/0091445 A1 | 5/2004 | Dykstra et al. | |
| 2005/0124530 A1 | 6/2005 | Creutz et al. | |
| 2005/0143282 A1 | 6/2005 | Creutz et al. | |
| 2006/0003913 A1 | 1/2006 | Boutique et al. | |
| 2007/0207942 A1 | 9/2007 | Creutz et al. | |
| 2008/0213191 A1 | 9/2008 | Scavone et al. | |
| 2008/0215023 A1* | 9/2008 | Scavone ............... | A61K 8/02 604/359 |
| 2011/0268778 A1 | 11/2011 | Dihora et al. | |
| 2011/0268802 A1 | 11/2011 | Dihora et al. | |
| 2011/0269657 A1 | 11/2011 | Dihora et al. | |
| 2011/0269658 A1 | 11/2011 | Dihora et al. | |
| 2012/0276210 A1 | 11/2012 | Dihora et al. | |
| 2014/0037703 A1 | 2/2014 | Dihora et al. | |
| 2014/0079747 A1 | 3/2014 | Dihora et al. | |
| 2014/0086965 A1 | 3/2014 | Dihora et al. | |
| 2014/0377207 A1* | 12/2014 | Scavone ............. | A61F 13/8405 424/76.5 |

FOREIGN PATENT DOCUMENTS

| | | |
|---|---|---|
| WO | WO-2003-015736 A2 | 2/2003 |
| WO | WO-2008-104690 A1 | 9/2008 |

OTHER PUBLICATIONS

U.S. Appl. No. 14/032,888, filed Sep. 20, 2013, Jianjun Justin Li et al.
U.S. Appl. No. 14/045,670, filed Oct. 3, 2013, Dihora et al.

* cited by examiner

*Primary Examiner* — Peter S Vasat
(74) *Attorney, Agent, or Firm* — George H. Leal; Andrew John Mueller

(57) ABSTRACT

An absorbent article selected from a sanitary napkin, an incontinence pad and a pantyliner, comprising a topsheet layer, a backsheet layer, a fastening adhesive applied on the backsheet garment facing surface. The adhesive comprises one or more thermoplastic elastomers. The article comprises a fragrance or odor control composition comprising one more esters, having a log P value of 2.9 or higher and a Kovats Retention Index of 1450 or higher, at least 90% of which are in encapsulated or complexed form.

12 Claims, No Drawings

ABSORBENT ARTICLE COMPRISING A FRAGRANCE OR ODOR CONTROL COMPOSITION

FIELD OF THE INVENTION

The present invention relates to an absorbent article comprising a fastening adhesive and an effective fragrance or odor control composition which does not alter the properties of the adhesive.

BACKGROUND OF THE INVENTION

Absorbent articles for personal hygiene which during use are attached to the underwear of the user by means of a fastening adhesive are known in the art. Typical examples include sanitary napkins, pantiliners and incontinence pads. Such articles are commonly used to absorb and retain bodily fluids and other exudates excreted by the human body, such as urine and menses. Typically, such exudates are perceived as malodorous and offensive. Therefore, methods and materials for controlling and reducing malodors in absorbent articles have been developed. Fragrance compositions have been widely used for this purpose in absorbent articles. Other compositions which may not properly be defined as "fragrance" compositions per se (because that they do not per se possess a pleasant odor) have also been used to reduce the perception of malodors. These are generally called "odor control compositions". Such compositions usually contain, sometimes along with conventional perfume ingredients, ingredients which are able to chemically react with the malodorant molecules released from the body fluids (such as amine group containing compounds or thiol group containing compounds) thus neutralizing the source of the malodor, and/or ingredients which are able to mask the source of the malodor Examples of such compositions are described in WO2007/113778 A2.

Fragrance and odor control compositions are usually formed by blends of organic compounds including aldehydes, ketones, esters, ethers, alcohols, essential oils, solvents and the like. It is well known that such organic compounds, when employed in absorbent articles, during storage of the absorbent articles, tend to migrate toward the backsheet and through it into the fastening adhesive. As a result, the properties of the fastening adhesive can be altered to the point that the adhesive is not effective anymore in keeping the product in place attached to the undergarments and/or in that the fastening adhesive leaves residues on the undergarments once the product is removed after use.

This problem is known in the art, an attempt in solving it is described e.g. in U.S. Pat. No. 4,237,591 describing an absorbent article wherein the perfume is immobilized on a fabric strip thus preventing its migration. Still this solution is not very effective in all cases, as most perfume ingredients are not locked in and can still migrate through the absorbent article. Also this solution adds complexity to the manufacturing process as it requires the use of "inert" materials like the fabric strip which are more difficult to handle.

Therefore a need still exist for an absorbent article comprising a fragrance or odor control composition and a fastening adhesive which is easy to manufacture using standard equipment and wherein the fastening adhesive is not affected, even upon prolonged storage, by the migration of the fragrance or odor control composition,

SUMMARY OF THE INVENTION

The present invention relates to an absorbent article selected from a sanitary napkin, an incontinence pad and a pantyliner, having a body-facing surface and a garment-facing surface, the absorbent article comprising:
  topsheet layer;
  backsheet layer;
  optionally one or more intermediate layers enclosed between said topsheet and said backsheet layers
  a fastening adhesive applied on said backsheet garment facing surface said adhesive comprising one or more thermoplastic elastomers
  a fragrance or odor control composition applied on or within at least one layer of said absorbent article,
wherein said fragrance or odor control composition comprises one more esters having a log P value of 2.9 or higher and a Kovats Retention Index (KI) of 1450 or higher and wherein at least 90% by weight of said one or more esters are comprised in encapsulated or complexed form.

The present invention also relates to a method of making an absorbent article selected from a sanitary napkin, an incontinence pad and a pantyliner, having a body-facing surface and a garment-facing surface, the absorbent article comprising:
  a topsheet layer;
  backsheet layer;
  optionally one or more intermediate layers enclosed between topsheet and backsheet
  a fastening adhesive applied on the backsheet garment facing surface said adhesive comprising one or more thermoplastic elastomer
the method comprising a step wherein, along the pad manufacturing line, a fragrance or odor control composition is applied directly on or within a layer of said absorbent article, and wherein said fragrance or odor control composition comprises one more esters having a log P value of 2.9 or higher and a Kovats Retention Index of 1450 or higher and wherein at least 90% by weight of said one or more esters are comprised in encapsulated or complexed form.

The absorbent article of the present invention exhibits no or very little degradation of the PFA even upon prolonged storage.

DETAILED DESCRIPTION OF THE INVENTION

"Absorbent article" refers to devices that absorb and contain body exudates, such as urine, menses, and feces. The term "disposable" is used herein to describe absorbent articles which are not intended to be laundered or otherwise restored or reused as an absorbent article after a single use. Examples of absorbent articles include diapers, toddler training pants, adult incontinence garments, and feminine hygiene garments such as sanitary napkins, pantiliners, interlabial devices, hemorrhoid pads, and the like. Absorbent articles according to the present invention are selected from sanitary napkins, incontinence pads and pantiliners.

Absorbent articles and components thereof according to the present invention, including the topsheet, backsheet, absorbent core, and any individual layers of these components, have a body-facing surface and a garment-facing surface. As used herein, "body-facing surface" means that surface of the article or component which is intended to be worn toward or adjacent to the body of the wearer, while the "garment-facing surface" is on the opposite side and is intended to be worn toward or placed adjacent to the wearer's undergarments when the disposable absorbent article is worn.

In general, the absorbent articles of the present invention typically comprise a topsheet, a backsheet, and (with the exception of thin pantyliners which are not meant to absorb fluids but just to provide a clean feeling to the panties) an absorbent core disposed between the topsheet and backsheet.

The topsheet of the absorbent hygienic article is preferably compliant, soft feeling, and non-irritating to the wearers skin and hair. Further, the topsheet is liquid pervious, permitting liquids (e.g., menses and/or urine) to readily penetrate through its thickness. A suitable topsheet may be manufactured from a wide range of materials such as woven and nonwoven materials (e.g., a nonwoven web of fibers), polymeric materials such as apertured formed thermoplastic films, apertured plastic films, and hydroformed thermoplastic films, porous foams, reticulated foams, reticulated thermoplastic films; and thermoplastic scrims. Suitable woven and nonwoven materials can be comprised of natural fibers (e.g., wood or cotton fibers), synthetic fibers (e.g., polymeric fibers such as polyester, polypropylene, or polyethylene fibers) or from a combination of natural and synthetic fibers. When the topsheet comprises a nonwoven web, the web may be manufactured by a wide number of known techniques. For example, the web may be spunbonded, carded, wet-laid, melt-blown, hydroentangled, combinations of the above, or the like.

The backsheet can be impervious to liquids (e.g., menses and/or urine) and can be preferably manufactured from a thin plastic film, although other flexible materials may also be used such as nonwovens. As used herein, the term "flexible" refers to materials which are compliant and will readily conform to the general shape and contours of the human body. The backsheet can prevent the exudates absorbed and contained in the absorbent core from wetting articles which contact the absorbent article such as bedsheets, pants, pajamas and undergarments. The backsheet can also be vapor permeable ("breathable"), while remaining fluid impermeable. The backsheet may comprise a woven or nonwoven material, polymeric films such as thermoplastic films of polyethylene or polypropylene, or composite materials such as a film-coated nonwoven material.

The backsheet and the topsheet can be positioned adjacent the garment surface and the body surface, respectively, of the absorbent core. The absorbent core can be joined with the topsheet, the backsheet, or both in any manner as is known by attachment means such as those well known in the art. Embodiments of the present invention are envisioned wherein portions of the entire absorbent core are unattached to either the topsheet, the backsheet, or both.

The absorbent core can be formed from any of the materials well known to those of ordinary skill in the art. Examples of such materials include multiple plies of creped cellulose wadding, fluffed cellulose fibers, wood pulp fibers also known as airfelt, textile fibers, a blend of fibers, a mass or batt of fibers, airlaid webs of fibers, a web of polymeric fibers, and a blend of polymeric fibers. Other suitable absorbent core materials include absorbent foams such as polyurethane foams or high internal phase emulsion ("HIPE") foams. Suitable HIPE foams are disclosed in U.S. Pat. Nos. 5,550,167, 5,387,207, 5,352,711, and 5,331,015.

For some absorbent articles, the absorbent core can be relatively thin, less than about 5 mm in thickness, or less than about 3 mm, or less than about 1 mm in thickness. Thickness can be determined by measuring the thickness at the midpoint along the longitudinal centerline of the pad by any means known in the art for doing while under a uniform pressure of 1.72 kPa.

The absorbent core can comprise superabsorbent materials such as absorbent gelling materials (AGM), including AGM fibers, as is known in the art. The absorbent core can therefore constitute a layer comprising superabsorbent material.

The absorbent article of the present invention can comprise other additional components, for example between the topsheet and absorbent core, such as a secondary topsheet or acquisition layer. The secondary topsheet or acquisition layer can comprise a tissue layer or a nonwoven, selected from for example carded resin-bonded nonwovens, embossed carded resin-bonded nonwovens, high-loft carded resin-bonded nonwovens, carded through-air-bonded nonwovens, carded thermo-bonded nonwovens, spunbonded nonwovens, and the like. A variety of fibers can be used in the secondary topsheet or acquisition layer, including natural fibers, e.g. wood pulp, cotton, wool, and the like, as well as biodegradable fibers, such as polylactic acid fibers, and synthetic fibers such as polyolefins (e.g., polyethylene and polypropylene), polyesters, polyamides, synthetic cellulosics (e.g., RAYON®, Lyocell), cellulose acetate, bicomponent fibers, and blends thereof. The basis weight of the secondary topsheet or acquisition layer can vary depending upon the desired application.

The absorbent article can comprise further components such as side cuffs, typically found in incontinence pads, and/or side wings or side flaps, typically found in sanitary napkins.

The absorbent articles herein are preferably disposable after a single use and are usually commercialized in packages comprising multiple units which in some cases can be individually wrapped.

The backsheet typically forms the garment facing surface of the absorbent article on which the fastening adhesive is placed. These adhesives are called panty fastening adhesives and will be normally referred to using the acronym PFA, common in the art. The PFAs are typically pressure sensitive and remain tacky well below their application temperature. The fastening adhesive in the present invention comprises at least one thermoplastic elastomer. Thermoplastic elastomers (also known as thermoplastic rubbers) are known in the art, are a class of copolymers or a physical mix of polymers (usually a plastic and a rubber) which consist of materials with both thermoplastic and elastomeric properties. They differ from most elastomers which are thermosets. It is believed, that their properties are due to weak crosslinking with hydrogen bonds as opposed to crosslinking with covalent bonding which occurs in thermoset elastomers.

Preferred thermoplastic elastomers in the present invention are styrene block copolymers, for example styrene isoprene styrene (SIS) or styrene butadiene styrene (SBS). In some embodiments the PFA comprises a tackifier, preferably a tackifier comprising esters, such as rosin esters. All embodiments can be advantageously also comprise a plasticizer, plasticizers are known in the art and are used to provide fluidity and easier handling of the adhesive when melt. Examples of plasticizers are waxes, oils such as mineral oil or vegetable oils or fats.

Preferably the PFA is a hot melt adhesive.

PFAs according to the present invention are effective in adhering to most undergarment substrates (both cotton and synthetics) with the right adhesion force so that the articles can be kept firmly in position and removed easily when needed without leaving residues.

Prior to use of the absorbent article, the areas being coated with PFA are typically protected from contamination and from adhering to another surface where this is not desired by a protective cover means such as a silicone coated release paper, a plastic film or any other easily removable cover. The protective cover means can be provided as a single piece or in a multitude of pieces, e.g. to cover the individual adhesive areas. It also can perform other functions such as provide individualised packaging for the article or provide a disposal function. Any commercially available release paper or film may be used. Suitable examples include BL 30 MG-A SILOX EI/O, BL 30 MG-A SILOX 4 P/O available from Akrosil Corporation, and M&W films available from Gronau in Germany, under the code X-5432.

The PFA may be applied to the garment-facing surface of the absorbent article, typically the backsheet and/or the wings using any one of methods well known in the art for this purpose such as slot coating, spraying and roll printing.

One method of applying the PFA to the garment-facing surface of the absorbent article is the direct coating on the backsheet; another method is printing the PFA onto a release paper, which is then pressed onto the garment-facing surface of the absorbent article. Thereby the PFA is transferred from the release paper to the garment-facing surface of the absorbent article. Such a procedure is described in EP 788,338.

It may be desirable that the PFA has a full surface coverage on the backsheet of the article or from 10 to 99%, or from 10 to 95%, or from 10 to 60% or from 15 to 50%.

In general, suitable components for the fragrance or odor control compositions include fragrance components and reactive components. Fragrance components are typically used in the field of perfumery to provide a composition with an aesthetically pleasing scent. Reactive components include components that can react with malodors, such as ammonia-based malodors or sulphur-based malodors (i.e. "malodor reactive components"), and components that mask malodors i.e. "malodor masking components"). Suitable reactive components are described, for example, in US 2008/0071238 A1 and WO 2007/113778 A2.

In terms of reactive components, those reacting with ammonia or malodorants sulphur compounds like thiols can be very effective in the present invention. Ammonia and thiols are two common components of malodor associated with the absorption bodily fluids, such as menses or urine. For example, ammonia is typically present in high amounts in absorbent products used for urine absorption due to degradation of urea.

Aldehydes and/or ketones can react with Ammonia and its derivatives to form imines (according to the so-called Schiff base reaction) or via Michael addition reactions.

Aldehydes and/or ketones can also react with thiols forming thioacetals or via Michael addition. In all cases the resulting compounds are non volatile and therefore essentially odorless.

Other components suitable herein are components that mask the malodors. This may occur through vapor pressure suppression of the malodor or by overwhelming the unpleasant malodor with the pleasant odor of the fragrance component. These materials, when used, may significantly reduce the ability to detect the malodors. The masking ability to hide malodors is possible due to the volatile nature of the materials selected, which are released from the complex or capsule in the absorbent article and are then inhaled into the nose of a consumer, generally within somewhat close range of the absorbent article, e.g. within about 0 to 10 meters of the article by normal breathing (although this should in no way be intended to limit the scope of the invention).

The components of the fragrance or odor control composition can also include fragrance components that impart an aesthetically pleasing odor character to the mixture.

It may be that for certain components, the same component can be considered both a malodor reactive component, a malodor masking component, and/or a fragrance component.

Compounds which can be used as reactive components, masking components and fragrance components are listed in the art e.g. in US 2008/0071238 A1 and WO 2007/113778 A2.

All these compounds can be used as liquids or in encapsulated/complexed form with the same type of encapsulation or complexation means which are described herein with reference to the esters of the present invention. The use of capsules or complexes will in general allow to protect the material and to trigger its release only at the moment it is needed the most such as for example when a gush of urine or menstrual fluid impacts the absorbent article. In some embodiments also a combination of free compounds and encapsulated and/or complexed compounds can be used.

The fragrance or odor control compositions can be applied in a variety of ways, and in a variety of patterns, to the absorbent article using conventional low viscous fluid application equipment which is well known to the skilled person such as spray, droplets or beads applicators. Such applicators allow to form any application pattern like stripes, circles, dots, drops, geometric figures, stars, decorative figures, irregular shapes, and the like. Also patterned applications are helpful because they allow a precise application so that it is easier to avoid contact with the aloe which connects the various layers of the absorbent article.

The fragrance or odor control compositions is typically disposed in the absorbent article in an amount of from about 0.01 to about 500 milligrams per absorbent article, from about 3 to about 200 milligrams per absorbent article or from about 4 to about 150 milligrams per absorbent article. In some embodiments where the absorbent article is selected from a sanitary napkin or a pantyliner the amount can be from about 0.04 to about 100 mg, in some embodiments where the absorbent article is an incontinence device the amount can be from about 1 to about 300 milligrams per absorbent article.

The fragrance or odor control composition in the present invention is applied on or within a layer of said absorbent article. This means that, since the absorbent article is constituted by a series of layers, the fragrance or odor control composition is applied onto one of the surfaces of these layers. Alternatively, if one of the layers allows it (because for example is a thick fibrous layer such as an absorbent core), the layer can be cut in two along a plane substantially parallel to the garment facing surface of the article and the fragrance or odor control composition can be applied on one of the two surfaces resulting from the cut and then the layer can be re-joined as a single layer.

In some embodiments the fragrance or odor control composition can be applied in a pattern. In these cases the fragrance or odor control composition is applied onto the surface of application with any possible application pattern: such as for example stripes, circles, dots, drops, geometric figures, stars, decorative figures, irregular shapes, and the like. In some cases it is possible that the fragrance or odor control composition is applied on more than one layer within the article. In that case, for the purpose of the present invention, the "pattern" of application of the fragrance or odor control composition will be considered as the combination of the various patterns projected on a plane parallel to garment facing surface of the article in a flattened configuration.

Similarly, in some embodiments also the PFA can be applied on the backsheet of the absorbent article in a pattern which can be selected from any possible application pattern such as for example stripes, circles, dots, geometric figures, stars, decorative figures, irregular shapes, and the like.

As mentioned above, among the desirable ingredients which are commonly used in fragrance or odor control compositions, esters play an important role. Many of the common ingredients used in fragrances as well as many ingredients which are active in masking malodors acting on nose receptors are esters. Also many low odor compounds used as solvents for other perfume ingredients which otherwise would not be miscible in the fragrance or odor control composition are esters. Some particular esters having a low volatility and relatively high hydrophobicity are particularly useful in the present invention as they are able to provide a sustained delivery for a long time and are particular effective as masking agents and are also useful in perfume compositions acting as solvents and preventing the evaporation of other ingredients. These particular esters are defined in the present invention as esters having a log P value of 2.9 or higher and a Kovats Retention Index of 1450 or higher. Among these, preferred esters are those having a log P value of 3 or higher and those having a Kovats Index of 1500 or higher.

The use of log P values is well known in the chemical arts as representing the relative affinity that a material has for partitioning between octanol and water, so that a material that partitions more readily into octanol would tend to be more lipophillic and have a higher log P value than a material that partitions less readily into octanol. Any method for measuring log P for a given substance should give comparable results, in case of doubts in the present invention log P values are obtainable using the method published by the United States Environmental Proetction Agency (EPA) published as OPPTS 830.7550, EPA 712-C-96-038 Aug. 1996, under the title "Product Properties Test Guidelines— OPPTS 830.7550 Partition Coefficient (n-Octanol/Water), Shake flask method." which description is incorporated herein by reference. In following this EPA method in all instances where a recommended procedure is described (such as number of rotations of the shaker) the recommended procedure should be followed. For the analytical determination of the substance in the two phases a skilled person will know what analytical method to use, gas chromatography (GC) can be preferably used, while HPLC can be used in case GC is not suitable.

Kovats Index as it is known in the art, is defined as the selective retention of perfume raw materials (PRMs) onto chromatographic columns based on the retention volume of the substance with respect to that to a homologous series of n-alkane standards.

The Kovats Index in the present application can be experimentally derived using an Agilent Technologies 6890 gas chromatogram with Flame Ionization Detector (FID), or equivalent using a DB-5 (5% phenyl-methylpolysiloxane) column 30 m×0.25 mm i.d., with a 0.25 micron film thickness available from Agilent Technologies. Chromatographic conditions are 1 mL/min of helium carrier with constant flow programming, a temperature program of 50° C. to 300° C. at 4 detector temperature 350° C., split injection at 300° C. Different chromatographic conditions may be required to achieve separation of the analytes of interest and can be readily adjusted by one skilled in the art. A linear alkane hydrocarbon standard mix (C8-C22 available from Aldrich Chemical Company or equivalent) is injected and the retention time for each component is recorded. The test sample (appropriately diluted in a suitable solvent) is injected under the same conditions, and the retention time for each component of interest is recorded. The Kovats Index under non-isothermal conditions is calculated for each component of interest in the test sample using the equation:

$$KI=100n+100[(t_{substance}-t_n)/(t_{n+1}-t_n)]$$

Where:
t=the uncorrected retention time of a peak
unknown=the peak of interest
n=the number of carbon atoms in the smaller alkane whose peak is adjacent to the peak of interest As known, a material's polarity, molecular weight, vapor pressure, boiling point, and the stationary phase property determine the extent of retention, and hence of the Kovats Index.

Examples of esters having a P value of 2.9 or higher and a Kovats Retention Index of 1450 or higher are the following esters:

| Ester | Log P | KI |
|---|---|---|
| Butyl salicylate | 3.58 | 1572.9 |
| Isoamyl salicylate | 3.74 | 1616.4 |
| Prenyl salicylate | 3.05 | 1655.3 |
| amyl salicylate | 4.09 | 1668.8 |
| n-Hexyl salicylate | 4.58 | 1765.1 |
| Helvetolide | 5.56 | 1773 |
| Cyclohexyl salicylate | 4.15 | 1821 |
| Phenyl salicylate | 3.49 | 1851.1 |
| Habanolide | 4.32 | 1862.9 |
| Exaltolide | 4.81 | 1882 |
| 2-Ethylhexyl salicylate | 4.92 | 1889.5 |
| Benzyl salicylate | 3.56 | 1920.3 |
| p-Cresyl salicylate | 4.06 | 1944.5 |
| Octyl salicylate | 5.38 | 1956.5 |
| trans-ambrettolide | 4.64 | 1961.1 |

Other esters which have a log P value of 2.9 or higher and a Kovats Retention Index of 1450 or higher can be found among citric acid esters, benzoic acid esters, cellulose esters, salicylic acid esters, lactic acid esters, acetic acid esters or acetates). Values of log P and KI for esters commonly used as fragrance ingredients are broadly available in the art, for example in the online database www.pherobase.com and in many others which are easily accessible and well known to the persons skilled in the art.

Also cyclic esters i.e. lactones are considered as "esters" for the purpose of the present invention.

It has been found that esters having a log P value of or higher and a Kovats Retention Index of 1450 or higher are more problematic than others when they migrate through the layers of the article and reach the fluid impervious backsheet and the PITA applied on its garment facing surface, both because they migrate more effectively and because they have a more detrimental effect on the properties of the adhesive, particularly when the PFA comprises thermoplastic elastomers according to the present invention.

The migration of these components of the fragrance or odor control composition may alter the characteristics of the backsheet and of the PFA glue. In particular the PFA tends to lose adherence with the backsheet so that undesirable residues of glue could be left onto the panties after usage of the article. In other cases the PFA may simply lose its function no that the absorbent article is not properly kept in place during use and/or the PFA may transfer to clothes and leave a residue that is difficult to remove.

This problem has been solved in the present invention by providing an article comprising a fragrance or odor control composition, said composition comprising one or more esters having a log P value of 2.9 or higher and a Kovats Retention Index of 1450 or higher and wherein at least 90% by weight of said one or more esters are comprised in encapsulated or complexed form. In some embodiments at least 95% of said one or more esters are comprised in encapsulated or complexed form, in other embodiments at least 99% of said one or more esters are comprised in encapsulated or complexed form. In some embodiments all said esters are comprised exclusively in encapsulated or complexed form.

In some embodiments the fragrance or odor control composition of the present invention comprises at least 10% or 15% or 20% by weight (based on the weight of the fragrance or odor control active ingredients only, i.e. not considering the encapsulating or complexing materials) of one more esters having a log P value of 2.9 or higher and a Kovats Retention Index (KI) of 1450 or higher. To note, the weight percentage of the compounds making up the fragrance or odor control composition of the present invention the encapsulating/complexing materials are not taken into account.

It has been found that by encapsulating or complexing selectively at least 90% by weight or 95% or 99% or even all of the esters belonging to the specific class of esters selected (those having a log P value of 2.9 or higher and a Kovats Retention Index (KI) of 1450 or higher) in a fragrance or odor control composition, absorbent articles having a PFA comprising thermoplastic elastomers could be made wherein the fragrance or odor control composition can perform its function and at the same time wherein the PFA degradation was prevented without affecting the character of the fragrance or odor control composition nor the stay in place performance of the article.

All percentages in the present application indicate weight percentages except where otherwise indicated.

All the embodiments described in the present application can be combined as apparent to a person skilled in the art. For example in each embodiment of an absorbent article according to the present invention which comprises a fragrance or odor control composition which composition comprises at least 10% or 15% or 20% by weight of one more esters having a log P value of 2.9 or higher and a Kovats Retention Index (KI) of 1450 or higher, said esters can be at least 90% by weight or 95% or 99% in encapsulated or complexed form.

Encapsulating Compounds

The esters of the present invention can be encapsulated using any technique known in the art. The term "Encapsulation" within the present invention is intended, to encompass any technology which allows introducing an ester according to the invention into an absorbent article as a solid in a mixture with other materials which are called in general "encapsulating materials". The esters when encapsulated are prevented from contacting other materials so to avoid unwanted reactions. Moreover, when encapsulated, their evaporation is prevented. Many types of capsules are known in the art and are used for the delivery of perfume ingredients. All these types of capsules are usable in the present invention. Capsules can have any size, typically used in the art and suitable herein are nanocapsules, microcapsules, and larger capsules. In general capsules will have a size such that their shorter diameter will be lower than 3 mm or lower than 1 mm.

Capsules allow the encapsulated composition to release when it is needed. Typically in the case of absorbent articles this corresponds to two cases:

1—when the article receives a liquid insult (e.g. when in absorbent hygienic articles menses or urine are discharged): in this case capsules comprise water soluble materials or materials which trigger release of the encapsulated compound when contacted with water or a water containing liquid.

2—when pressure or force is exerted on the article (e.g. in the case when an absorbent hygienic article is worn during a period of high activity): in this case, for example, breakable capsules having a shell of rupturable polymeric film can be used.

All these types of capsule are known in the art e.g. as perfume delivery systems.

These two cases should however be intended as non limiting examples. In fact any other trigger (or combination of triggers) can be used to release the encapsulated compound from the capsule, e.g. evaporation, diffusion, temperature, humidity, light etc. The release of the encapsulated compound can be instantaneous or sustained over time, depending on needs. The skilled person, based on the desired trigger action and release type, will be able to select the appropriate encapsulating material from those known in the art.

Capsules can use different encapsulating materials:

I. Polymers.

Polymeric materials can be used as encapsulating materials.

Classical coacervates, water soluble or partly soluble to insoluble charged or neutral polymers, liquid crystals, hot melts, hydrogels, perfumed plastics, microcapsules, nano- and micro-latexes, polymeric film formers, and polymeric absorbents, polymeric adsorbents, etc. are some examples. Polymeric capsules include but are not limited to:

a.) Matrix Systems: The compound to be encapsulated is dissolved or dispersed in a polymer matrix or particle. Such compounds, for example, may be dispersed into the polymer prior to formulating into the product. Diffusion of the encapsulated compound from the polymer is a common trigger that allows or increases the rate of compound release from a polymeric matrix system that is deposited or applied to the desired surface, although many other triggers are know that may control compound release. Absorption and/or adsorption into or onto polymeric particles, films, solutions, and the like are aspects of this technology. Nano- or micro-particles composed of organic materials (e.g., latexes) are examples. Suitable particles which can be used herein include a wide range of materials including, but not limited to polyacetal, polyacrylate, polyacrylic, polyacrylonitrile, polyamide, polyaryletherketone, polybutadiene, polybutylene, polybutylene terephthalate, polychloroprene, poly ethylene, polyethylene terephthalate, polycyclohexylene dimethylene terephthalate, polycarbonate, polychloroprene, polyhydroxyalkanoate, polyketone, polyester, polyethylene, polyetherimide, polyethersulfone, polyethylenechlorinates, polyimide, polyisoprene, polylactic acid, polymethylpentene, polyphenylene oxide, polyphenylene sulfide, polyphthalamide, polypropylene, polystyrene, polysulfone, polyvinyl acetate, polyvinyl chloride, as well as polymers or copolymers based on acrylonitrilebutadiene, cellulose acetate, ethylene-vinyl acetate, ethylene vinyl alcohol, styrene-butadiene, vinyl acetate-ethylene, and mixtures thereof.

"Standard" systems refer to those that are "pre-loaded" with the intent of keeping the pre-loaded compound associated with the polymer until the moment or moments of release. Such polymers may also suppress the neat product odor and provide a bloom and/or longevity benefit depending on the rate of compound release. One challenge with such systems is to achieve the ideal balance between 1) in-product stability (keeping the compound inside carrier until you need it) and 2) timely release (during use. Suitable micro-particles and micro-latexes as well as methods of making same may be found in USPA 2005/0003980 A1. Matrix systems also include hot melt adhesives and perfumed plastics. Polymer Assisted Delivery (PAD) matrix systems may include those described in the following references: US Patent Applications 2004/0110648 A1; 2004/0092414 A1; 2004/0091445 A1 and 2004/0087476 A1; and U.S. Pat. Nos. 6,531,444; 6,024,943; 6,042,792; 6,051,540; 4,540,721 and 4,973,422.

Silicones are also examples of polymers that may be used as encapsulating materials and can provide compound release benefits. Suitable silicones as well as making same may be found in WO 2005/102261; USPA 2005/0124530A1; USPA 2005/0143282A1; and WO 2003/015736. Functionalized silicones may also be used as described in USPA 2006/003913 A1. Examples of silicones include polydimethylsiloxane and polyalkyldimethylsiloxanes.

b.) Reservoir Systems: Reservoir systems are also known as a core-shell type technology, in which the compound to be released is surrounded by a release controlling membrane, which serves as a protective shell. The material inside the capsule is referred to as the core, internal phase, or fill, whereas the wall is sometimes called a shell, coating, or membrane. Depending on the type of shell materials the capsules can be activated by different mechanisms, for example the coating can be soluble in water or soluble in water solutions having a certain pH. In certain embodiments of the present invention the reservoir capsules have water insoluble shells and the core of the capsule is released upon mechanical activation.

Pressure sensitive capsules or friable capsules are examples of this technology. Friable capsules can be made in any sizes, and shapes, typically used are friable microcapsules. Any type of polymeric material can be used to make the shell of friable capsules, as well as any material can be used as a core material as known in the art. A skilled person will be able to determine which materials can be used to encapsulate certain core materials based on the knowledge available in the art concerning the compatibility of the materials (e.g. in general the shell material is selected so that core material will not act as a solvent on it.) Friable MICROcapsules will be described Bow in more detail, it is clear to the skilled person that the same type of materials and construction can be used to make larger or smaller capsules.

Friable microcapsules are capsules where the outer shell is made from any polymer or mixture of polymers. Typical polymers which can be used to be comprised in the shell of a friable microcapsule include melamine-formaldehyde or urea-formaldehyde condensates, melamine-resorcinol or urea-resorcinol condensates, nylon, polyacrylates, polyethylenes, polyamides, polyamides, polystyrenes, polyisoprenes, polycarbonates, polyesters, polyureas, polyurethanes, polyolefins, polysaccharides, epoxy resins, vinyl polymers, silk, wool, gelatin, cellulose, proteins and mixture thereof as well as co-polymers comprising, as co monomers, monomers contained in these mentioned polymers.

Among the most stable friable microcapsules are those comprising polyoxymethyleneurea (PMU)-based polymers, melamine-formaldehyde based polymers, and polyacrylate based polymers.

In some embodiments the microcapsule outer shell material can include a polyacyrylate material. Any polymer or copolymer including acrylate or metacrylate monomers can be used in the present invention, preferred materials are those known in the art as forming polyacrylate microcapsules such as, for example, those described in US 2012-276210A1. In some embodiment the shell of the microcapsules comprises a polyacrylate copolymer, in some case can be a polyacrylate random copolymer.

A friable microcapsule is configured to release its core substance when its outer shell is ruptured. The rupture can be caused by forces applied to the outer shell during mechanical interactions. Friable microcapsules can have various fracture strengths. Each microcapsule can have an outer shell with a fracture strength of 0.2-10.0 mega Pascals, when measured according to the Fracture Strength Test Method, described in co-pending application U.S. 61/703,587. As an example, a microcapsule can have an outer shell with a fracture strength of 0.2-2.0 mega Pascals.

Friable microcapsules can have various core to outer shell ratios. Each microcapsule has an outer shell, and a core within the outer shell, and a core to outer shell ratio (in weight) from 99-1 to 1-99, or from 95-5 to 10-90, or from 50-50 to 90-10.

Friable microcapsules can have various outer shell thicknesses. In some embodiments the microcapsule can have an outer shell with an overall thickness of 1-300 nanometers or 2-200 nanometers.

For application to an anhydrous product such as an absorbent article, it is especially preferred that the microcapsule is applied as an anhydrous particle. Such particles may be produced by spray drying as describe in patent application U.S. 61/703,616. In the instances where friable microcapsules are spray dried, it is preferable to apply these particles in a paste or slurry comprising a carrier vehicle. These particles may also be directly applied to the substrate as a powder without using a carrier vehicle. Alternately, the friable microcapsules can be delivered via an aqueous slurry to surfaces of the absorbent article and allowed to dry.

Friable microcapsules and relative methods for making them as well as methods to measure their properties which can be used herein are described in co-pending applications U.S. 61/703,616 and U.S. 61/703,587, which are incorporated herein by reference.

Example methods for making polyacrylate microcapsules are disclosed in U.S. Patent Application 61/328,949; U.S. Patent Application 61/328,954; U.S. Patent Application 61/328,962; and U.S. Patent Application 61/328,967 which are incorporated herein by reference.

II. Starches:

The use of a starch encapsulation technology allows one to modify the properties of the compound to be encapsulated, for example, by converting a liquid compound into a solid by adding ingredients such as starch. The benefit includes increased retention for volatile compounds during product storage. Upon exposure to moisture, a release may be triggered. Another benefit is that the starch encapsulation allows the product formulator to select compounds or concentration of compounds that normally cannot be used without the presence of starch encapsulation. Suitable starch encapsulation examples as well as methods of making the same may be found in US 2005/0003980 A1 and U.S. Pat. No. 6,458,754 B1.

In one aspect, starch encapsulated compounds may be made by preparing a mixture comprising starch, water, acid and the compound(s) which need to be encapsulated, the acid being incorporated in the mixture in an amount sufficient to lower the pH of the starch-water mixture by at least 0.25 units; and spray drying the mixture thereby forming the encapsulated compound(s). In the first step in the process of compound(s) encapsulation, an aqueous mixture is prepared comprising starch, water, the compound(s) which need to be encapsulated and acid. These ingredients may be added in any order, but usually the starch-water mixture is prepared first and subsequently, either sequentially or together, the acid and compound(s) to encapsulate are added. When they are added sequentially, the acid may be added prior to the ingredient for encapsulation. Alternatively, the acid is added after the ingredient for encapsulation. The concentration of starch in the aqueous mixture may be from as low as 5 or 10 wt % to as high as 60 or even 75 wt %. Generally the concentration of starch in the mixture is from 20 to 50 wt %, more usually around 25 to 40 wt % in the aqueous mixture.

Suitable starches can be made from raw starch, pregelatinized starch, modified starch derived from tubers, legumes, cereal and grains for example corn starch, wheat starch, rice starch, waxy corn starch, oat starch, cassava starch, waxy barley starch, waxy rice starch, sweet rice starch, amioca, potato starch, tapioca starch and mixtures thereof. Modified starches may be particularly suitable for use in the present invention, and these include hydrolyzed starch, acid thinned starch, starch having hydrophobic groups, such as starch esters of long chain hydrocarbons ($C_5$ or greater), starch acetates, starch octenyl succinate and mixtures thereof. In one aspect, starch esters, such as starch octenyl succinates are employed.

The term "hydrolyzed starch" refers to oligosaccharide-type materials that are typically obtained by acid and/or enzymatic hydrolysis of starches, preferably corn starch. It may be preferred to include in the starch water-mixture, a starch ester. Particularly preferred are the modified starches comprising a starch derivative containing a hydrophobic group or both a hydrophobic and a hydrophilic group which has been degraded by at least one enzyme capable of cleaving the 1,4 linkages of the starch molecule from the non-reducing ends to produce short chained saccharides to provide high oxidation resistance while maintaining substantially high molecular weight portions of the starch base. The aqueous starch mixture may also include a plasticizer for the starch. Suitable examples include monosaccharides, disaccharides, oligosaccharides and maltodextrins, such as glucose, sucrose, sorbitol, gum arabic, guar gums and maltodextrin.

The acid used in the process of the invention may be any acid. Examples include sulfuric acid, nitric acid, hydrochloric acid, sulfamic acid and phosphonic acid. In one aspect, carboxylic organic acids are employed. In another aspect, organic acids comprising more than one carboxylic acid groups are employed. Examples of suitable organic acids include citric acid, tartaric acid, maleic acid, malic acid, succinic acid, sebacic acid, adipic acid, itaconic acid, acetic acid and ascorbic acid, etc. In one aspect, saturated acids, such as citric acid, are employed.

Following the formation of the aqueous mixture comprising starch, water, perfumes and acid, the mixture is mixed under high shear to form an emulsion or dispersion of ingredient for encapsulation in the aqueous starch solution.

Any suitable technique may then be used for the final stage of processing where the aqueous mixture including acid and perfumes is atomized and dried. Suitable techniques include, but are not limited to those known in the art including spray drying, extrusion, spray chilling/crystallization methods, fluid bed coating and the use of phase transfer catalysts to promote interfacial polymerization. Spray efficiencies may be increased by methods known in the art, such as by using high drying towers, lightly oiling the chamber walls, or using preconditioned air in which the moisture has been substantially removed.

Coated Capsules

In some embodiments the primary materials forming the capsule as described so far, may be further encapsulated with a secondary coating material. Any of the capsule types mentioned so far can be used in the present invention as such or with an additional secondary coating material.

An additional secondary coating material can help in reducing the scent perception, in reducing evaporation of volatile components over time (especially at elevated temperatures and humidity conditions) and in increasing chemical stability of the complexed compound by reducing the exposure of the complexed compounds (which in the present invention comprise highly reactive materials) to prematurely react or decompose so they are no longer functional or have a different odor character when activated. Additionally the use of coated capsules can allow altering the release characteristic of the encapsulated material (slowing or accelerating its release, or changing the release trigger, for example introducing a pH trigger). Generally, any second material that is added to or applied directly to a primary encapsulating material that accomplishes one or more of the above functions is characterized as a coating. The secondary coating may be directly applied using a second process step following creation of the primary capsule, using a process such as prilling, or using any fluidized bed process to apply a secondary surface coating (for example a Wurster Coater).

Coating compositions which are suitable for the present invention are all capsule coating compositions which are commonly known in the art. These include for example: polysaccharides (for example, but not limited to unmodified starch, chemically modified starch, dextrins, cyclodextrin and cyclodextrin derivatives), natural and artificial/synthetic waxes, esters and ester derivatives, fatty acids, natural and synthetic and chemically modified lipids, fatty alcohols, hydrocarbons (liner or branched, petrolatum), enteric coating compositions (such as the Eudragit series of Methacrylic acid co-polymers), polyvinyl alcohols, polyethylene glycols, silicones (for example, but not limited to silicone copolymers and functionalized silicones), surfactants, emulsifiers, polypropylene glycols, cellulose derivatives (methyl cellulose, hydroxypropyl cellulose), glycerin, mono and diglycerides, polyglycerol and polyglycerol esters and emulsifiers employed in food applications.

An example of the preparation of a coated capsule which can be used in the present invention has been described in U.S. Pat. No. 4,973,422 (see in particular Example 2).

Complexed Compounds

For "complex" it is intended an "inclusion complex" within the meaning of IUPAC Compendium of Chemical Terminology 2nd Edition (1997) wherein the complexing agent is the host and the complexed compound is the "guest". Examples of complexing agents are cyclodextrins. As used herein, the term "cyclodextrin" includes any of the known cyclodextrins such as substituted and unsubstituted cyclodextrins containing from about six to about twelve glucose units, for example alpha-cyclodextrin, beta-cyclodextrin, gamma-cyclodextrin and/or their derivatives and/or mixtures thereof. For example, the cyclodextrin complex of the present invention can comprise cyclodextrin selected from the group consisting of beta-cyclodextrin, alpha-cyclodextrin, hydroxypropyl alpha-cyclodextrin, hydroxypropyl beta-cyclodextrin, methylated-alpha-cyclodextrin, methylated-beta-cyclodextrin, and mixtures thereof. Cyclodextrin complexes of compounds which are active against malodors can be prepared as known in the art for example using the kneading method described in U.S. Pat. No. 5,571,782 and U.S. Pat. No. 5,543,157 or, preferably, using the spray drying method described in WO2008/104690A2.

In some embodiment of the present invention the application pattern of the fragrance or odor control composition and the application pattern of the PFA do not overlap for more than for 3% of the total surface of the backsheet of the article when the absorbent article is in a flattened configuration and said patterns are seen along a direction perpendicular to the garment facing surface of the article.

For "pattern of application" of a material on a surface we indicate the parts of that surface which are in contact with the material, in this case the fragrance or odor control composition and the fastening adhesive respectively.

For "to overlap" it is meant "to be in the optical path" of an observer which observes along a direction perpendicular to said garment facing surface of the article (like the moon overlaps the sun in a solar eclipse).

For "total surface of the backsheet" it is intended e total surface of the backsheet of the absorbent article including the wings if present.

In some embodiments of the present invention the application pattern of the fragrance or odor control composition and the application pattern of the PFA do not overlap for more than for 3% of the total surface of the article or more than 1% or more than 0.1%.

In another embodiment the application pattern of the fragrance or odor control composition and the application pattern of the PFA do not overlap at all.

It has also been surprisingly found that, when the absorbent article comprises an absorbent layer which comprises a superabsorbent material such as an absorbent gelling material (AGM) the migration of components from the fragrance or odor control composition toward the backsheet is further reduced. Without being bound by theory it is believed this is due to the fact that the esters are at least partially absorbed by the AGM.

The present invention further encompasses a method for manufacturing an absorbent article selected from a sanitary napkin, an incontinence pad and a pantyliner, the article having a body-facing surface and a garment-facing surface and comprising:
 a topsheet layer;
 a backsheet layer;
 optionally one or more intermediate layers enclosed between topsheet and said backsheet
 a fastening adhesive applied on the backsheet garment facing surface said adhesive comprising one or more thermoplastic elastomer.

Absorbent articles of this type are normally made by combining the various layers making up the article on a conveyor belt. The method according to the present invention comprises a step wherein, along the manufacturing line when the layers are combined, a fragrance or odor control composition is applied directly on or within a layer of said absorbent article, wherein said fragrance or odor control composition comprises one more esters having a log P value of 2.9 or higher and a Kovats Retention Index of 1450 or higher and wherein at least 90% by weight said one or more esters are comprised in encapsulated or complexed form.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. An absorbent article selected from a sanitary napkin, an incontinence pad and a pantyliner, the absorbent article having a body-facing surface and a garment-facing surface, said absorbent article comprising:
 a topsheet layer;
 a backsheet layer;
 optionally one or more intermediate layers enclosed between said topsheet and said backsheet
 a fastening adhesive applied on the backsheet garment facing surface said adhesive comprising one or more thermoplastic elastomers
 a fragrance or odor control composition applied on or within at least one layer of said absorbent article,
wherein said fragrance or odor control composition comprises one more esters having a log P value of 2.9 or higher and a Kovats Retention Index of 1450 or higher, wherein at least 90% by weight of said one or more esters are comprised in encapsulated or complexed form.

2. The absorbent article of claim 1, wherein all of said one or more esters are comprised in encapsulated or complexed form.

3. The absorbent article of claim 1, wherein said fragrance or odor control composition comprises at least 10% by weight, based on the weight of the fragrance or odor control active ingredients only, of one more esters having a log P value of 2.9 or higher and a Kovats Retention Index of 1450 or higher.

4. The absorbent article of claim 1, wherein said one or more thermoplastic elastomer comprises styrene block copolymers.

5. The absorbent article of claim 1, wherein said fastening adhesive is a hot melt adhesive.

6. The absorbent article of claim 1, wherein said fragrance or odor control composition comprises one or more esters that have a log P value of 3 or higher.

7. The absorbent article of claim 1, wherein said fragrance or odor control composition comprises one or more esters having a Kovats Retention Index of 1500 or higher.

8. The absorbent article of claim 1, wherein said one or more esters are starch encapsulated.

9. The absorbent article of claim 1, wherein said one or more esters are present as cyclodextrin complexes.

10. The absorbent article of claim 1, wherein said fastening adhesive and said fragrance or odor control composition are applied in patterns which do not overlap for more than 3% of the total surface of the backsheet when the absorbent article is in a flattened configuration and said patterns are seen along a direction perpendicular to said body facing and garment facing surfaces of the article.

11. The absorbent article of claim 1, further comprising said one or more intermediate layers wherein at least one of said one or more intermediate layers is an absorbent layer comprising a superabsorbent material.

12. A method for manufacturing an absorbent article selected from a sanitary napkin, an incontinence pad and a pantyliner, said article having a body-facing surface and a garment-facing surface, said absorbent article comprising:
    a topsheet layer;
    a backsheet layer;
    optionally one or more intermediate layers enclosed between said topsheet and said backsheet
    a fastening adhesive applied on the backsheet garment facing surface said adhesive comprising one or more thermoplastic elastomers
    said method comprising a step wherein, along the pad manufacturing line, a fragrance or odor control composition is applied on or within at least one layer of said absorbent article,
wherein said fragrance or odor control composition comprises one more esters having a log P value of 2.9 or higher and a Kovats Retention Index of 1450 or higher and wherein at least 90% by weight of said one or more esters are comprised in encapsulated or complexed form.

* * * * *